United States Patent
Von Arx et al.

(10) Patent No.: US 7,844,341 B2
(45) Date of Patent: Nov. 30, 2010

(54) IMPLANTABLE MEDICAL DEVICE WITH ANTENNA

(75) Inventors: Jeffrey Allen Von Arx, Minneapolis, MN (US); Prashant B. Rawat, Blaine, MN (US); Daniel Kollman, Andover, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/354,375

(22) Filed: Jan. 15, 2009

(65) Prior Publication Data

US 2009/0182426 A1     Jul. 16, 2009

Related U.S. Application Data

(60) Provisional application No. 61/021,202, filed on Jan. 15, 2008.

(51) Int. Cl.
*A61N 1/08* (2006.01)
(52) U.S. Cl. .......................................... 607/60
(58) Field of Classification Search ............. 607/30–32, 607/36–37, 59–60
See application file for complete search history.

(56) References Cited

U.S. PATENT DOCUMENTS

| | | | |
|---|---|---|---|
| 5,179,945 A | 1/1993 | Van Hofwegen et al. | |
| 5,733,313 A | 3/1998 | Barreras, Sr. et al. | |
| 6,075,488 A | 6/2000 | Hope | |
| 6,083,248 A * | 7/2000 | Thompson | 607/30 |
| 6,272,379 B1 | 8/2001 | Fischell et al. | |
| 6,456,256 B1 | 9/2002 | Amundson et al. | |
| 6,470,215 B1 * | 10/2002 | Kraus et al. | 607/60 |
| 6,497,655 B1 | 12/2002 | Linberg et al. | |
| 6,553,263 B1 | 4/2003 | Meadows et al. | |
| 6,614,406 B2 * | 9/2003 | Amundson et al. | 343/873 |
| 6,668,751 B1 | 12/2003 | Henke | |
| 6,738,671 B2 | 5/2004 | Christophersom et al. | |
| 6,763,269 B2 * | 7/2004 | Cox | 607/60 |
| 6,809,701 B2 | 10/2004 | Amundson et al. | |
| 6,957,107 B2 | 10/2005 | Rogers et al. | |

(Continued)

FOREIGN PATENT DOCUMENTS

WO     WO-03095024     11/2003

OTHER PUBLICATIONS

"Antenna tuner", Wikipeida, the free encyclopedia, http://en.wikipedia.org/wiki/Antenna_tuner (Oct. 31, 2007).

(Continued)

*Primary Examiner*—Carl H Layno
*Assistant Examiner*—Paula J Stice
(74) *Attorney, Agent, or Firm*—Pauley, DeVries Smith & Deffner, L.L.C.

(57) ABSTRACT

An implantable medical device for use in a patient management system is described including a sensor, a processor, and a first communications unit. The first communications unit can deliver notification of significant events to a host computer using a short-range telemetry first communications link. A second communications unit can deliver notification of the significant events to the host computer over a second communications link, which is over a pervasive wireless communications network, such as a cell phone network. The device includes an antenna that is operatively connected to both the first and second communications units.

22 Claims, 6 Drawing Sheets

U.S. PATENT DOCUMENTS

| | | |
|---|---|---|
| 6,980,112 B2 | 12/2005 | Nee |
| 6,985,698 B2 | 1/2006 | Aggarwal et al. |
| 6,985,771 B2 | 1/2006 | Fischell et al. |
| 6,985,773 B2 | 1/2006 | Von Arx et al. |
| 7,027,871 B2 * | 4/2006 | Burnes et al. .................. 607/60 |
| 7,047,076 B1 * | 5/2006 | Li et al. ......................... 607/36 |
| 7,060,030 B2 | 6/2006 | Von Arx et al. |
| 7,228,182 B2 | 6/2007 | Healy et al. |
| 7,283,874 B2 | 10/2007 | Penner |
| 2003/0088295 A1 | 5/2003 | Cox |
| 2003/0114897 A1 | 6/2003 | Von Arx et al. |
| 2003/0149459 A1 | 8/2003 | Von Arx et al. |
| 2004/0122489 A1 | 6/2004 | Mazar et al. |
| 2004/0204744 A1 | 10/2004 | Penner et al. |
| 2005/0027329 A1 | 2/2005 | Holmquist et al. |
| 2005/0027330 A1 * | 2/2005 | Govari ......................... 607/60 |
| 2005/0137648 A1 | 6/2005 | Cosendai et al. |
| 2005/0240245 A1 | 10/2005 | Bange et al. |
| 2005/0288738 A1 | 12/2005 | Bange et al. |
| 2006/0009818 A1 | 1/2006 | Von Arx et al. |
| 2006/0030903 A1 * | 2/2006 | Seeberger et al. ............. 607/60 |
| 2006/0161222 A1 * | 7/2006 | Haubrich et al. .............. 607/60 |
| 2006/0221902 A1 | 10/2006 | Chen et al. |
| 2007/0030116 A1 | 2/2007 | Feher |
| 2007/0100385 A1 * | 5/2007 | Rawat et al. .................. 607/37 |
| 2007/0239229 A1 | 10/2007 | Masoud et al. |
| 2008/0103555 A1 * | 5/2008 | Dicks et al. ................... 607/60 |

OTHER PUBLICATIONS

"Balun", Wikipeida, the free encyclopedia, http://en.wikipedia.org/wiki/Balun (Oct. 31, 2007).

"GSM frequency bands", Wikipeida, the free encyclopedia, http://en.wikipedia.org/wiki/GSM_frequency_ranges (Nov. 1, 2007).

"Impedance matching", Wikipeida, the free encyclopedia, http://en.wikipedia.org/wiki/Impedance_matching (Oct. 31, 2007).

Francis et al., "Interference Between Cellular Telephones and Implantable Rhythm Devices: A Review on Recent Papers", *Indian Pacing and Electrophysiology Journal*, 6(4):226-233 (2006).

Lau et al., "Impact of Matching Network on Bandwidth of Compact Antenna Arrays", *IEEE Transaction on Antennas and Propagation*, 54(11):3225-3238.

Mendelsohn, "Review: Body Area Network gets under your skin", Product Center, http://www.eeproductcenter.com/showArticle.jhtml?arfticleID=199500535 (Oct. 31, 2007).

PCT International Search Report and Written Opinion from International Application No. PCT/US2009/031134, corresponding to U.S. Appl. No. 12/354,490, mailed Apr. 21, 2009 (16 pages).

PCT International Search Report and Written Opinion from International Application No. PCT/US2009/031135, corresponding to U.S. Appl. No. 12/354,375, mailed Apr. 21, 2009 (14 pages).

Rhea, "The Yin-Yang of Matching: Part 2—Practical Matching Techniques", *High Frequency Electronics*, pp. 28-40 (2006).

Sivard et al., "The Challenge of designing in-body communications", Embedded Systems Design, http://www.embedded.com/columns/technicalinsights/51200651?_requestid=918377 (Oct. 26, 2004).

Wilson, "How Cell-phone Implants Work", http://electronics.howstuffworks.com/cell-phone-implant.htm/printable (Jun. 11, 2007).

* cited by examiner

IMPLANTABLE MEDICAL DEVICE WITH ANTENNA

This application claims the benefit of U.S. Provisional Application No. 61/021,202, filed Jan. 15, 2008, the contents of which are herein incorporated by reference.

TECHNICAL FIELD

This application relates generally to patient management systems, and particularly, but not by way of limitation, to an implantable medical device having wireless communication capabilities and configured for use in a patient management system.

BACKGROUND OF THE INVENTION

Patient treatment for heart conditions often occurs only after an adverse event such as acutely de-compensated heart failure resulting in hospitalization. However, patients may be provided with an implanted medical device (IMD) to monitor for signs of impending de-compensation and other problems. IMDs can also provide electrical pacing therapy to treat impending de-compensation and other problems. IMDs can measure and record electrical cardiac activity, physical motion and other clinical parameters.

The data collected by these devices can be retrieved from the device. In a typical configuration, an IMD is provided with an antenna for communicating by telemetry with a device outside of the patient's body. In one case, the device outside of the patient's body is a wand that is held against or near the patient's body in the vicinity of the implanted device. The wand is conventionally magnetically or inductively coupled to the IMD and is wired to a programmer and recorder module that receives and analyzes the information from the implanted device and that may provide an interface for a person such as a physician to review the information. The programmer and recorder module is in turn connected to a host computer which is monitored by medical professionals.

In other cases, an IMD has far-field RF telemetry capabilities, so that the IMD can communicate with a monitoring unit in the patient's home without requiring any action by the patient. It is not necessary for a patient to place a wand near the implanted device in these systems. The IMD communicates with a repeater located in the patient's home via a far field wireless communications link. For example, one known RF communication system for these short-range distances is the LATITUDE® Advanced Patient Management system sold by Boston Scientific Corporation of St. Paul, Minn. Such a system usually includes a patient monitor device that can receive transmissions from an IMD from within about 9 to 12 feet. In one known arrangement, a patient places a patient monitor device in a living space, such as on a stand next to the patient's bed, so that the patient monitor device can receive data transmitted from the IMD while the patient is in proximity to the monitor device. The patient monitor device is connected to a host computer that is monitored by medical professionals.

While the use of a patient monitor unit is convenient for a patient while located near the repeater, such as within 9 to 12 feet, no data can be transmitted from the implanted device to the repeater if the implanted device is out of range. If a medically significant event occurs while the implanted device is out of range of the repeater, it will not be possible to transmit information about the medically significant event back to the host computer at that time.

IMDs provided to heart failure patients frequently are also capable of electronic signal processing to deliver a medical therapy. One example of a type of implantable medical device is a cardiac rhythm management (CRM) device. CRM devices may include, for example, cardiac resynchronization devices, pacemakers and implantable cardioverter defibrillators (ICD). These devices generally provide medical treatment to a patient having a disorder relating to the pacing of the heart, such as bradycardia or tachycardia. For example, a patient having bradycardia may be fitted with a pacemaker, where the pacemaker is configured to monitor the patient's heart rate and to provide an electrical pacing pulse to the cardiac tissue if the heart fails to naturally produce a heart beat at a sufficient rate. By way of further example, a patient may have an ICD implanted to provide an electrical defibrillation shock to the patient's heart if the patient experiences fibrillation.

IMDs may further be configured to receive instructions from an external source to modify and control the operation of the IMD. For example, a physician may transmit instructions from an external device to an implanted medical device within a patient to change the therapy administered to the patient in response to the physician's analysis of information received about the patient's condition.

Improved systems for communications of signals to and from implantable medical devices are needed, especially while the patient is not in range of a home monitoring unit.

SUMMARY OF THE INVENTION

In one embodiment, an implantable medical device for use in a patient management system includes a sensor capable of measuring a body characteristic and generating a data signal describing the measurement and a processor configured to analyze the data signal and configured to identify one or more significant events that warrant attention for the well-being of a patient. The implantable medical device also includes a first communications unit including a first wireless transmitter/receiver capable of establishing a first communications link with a host computer using an external local transmitter/receiver unit, when it is within a short-range telemetry communication range of the local transmitter/receiver unit, to deliver at least notification of the one or more significant events to said host computer using said first communications link. The implantable medical device further includes a second communications unit comprising a second wireless transmitter/receiver unit capable of establishing a second communications link with the host computer over a pervasive wireless communications network to deliver at least notification of the one or more significant events to said host computer over the second communications link. The implantable medical device further includes an antenna operatively connected to both the first and second communications unit.

In another embodiment, a method of telemetry between an implantable medical device used in a patient management system and a host computer includes providing an implantable medical device including a sensor and an antenna, and measuring a body characteristic using the sensor and generating a data signal that describes the measurement. The method further includes analyzing the data signal and identifying one or more significant events that merit attention. Notification of the one or more significant events is wirelessly transmitted over the antenna by a first communication unit from the implantable medical device to an external local transmitter/receiver unit in the host computer over a first communications link, when the implantable medical device is within a short-range telemetry communication range of said local transmitter/receiver unit. When the implantable medical device is out of range of the local transmitter/receiver unit, notification of the one or more significant events from the implantable medical device is wirelessly transmitted over the antenna to the host computer by a second communications unit over a pervasive wireless communications network.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

Figure 1:
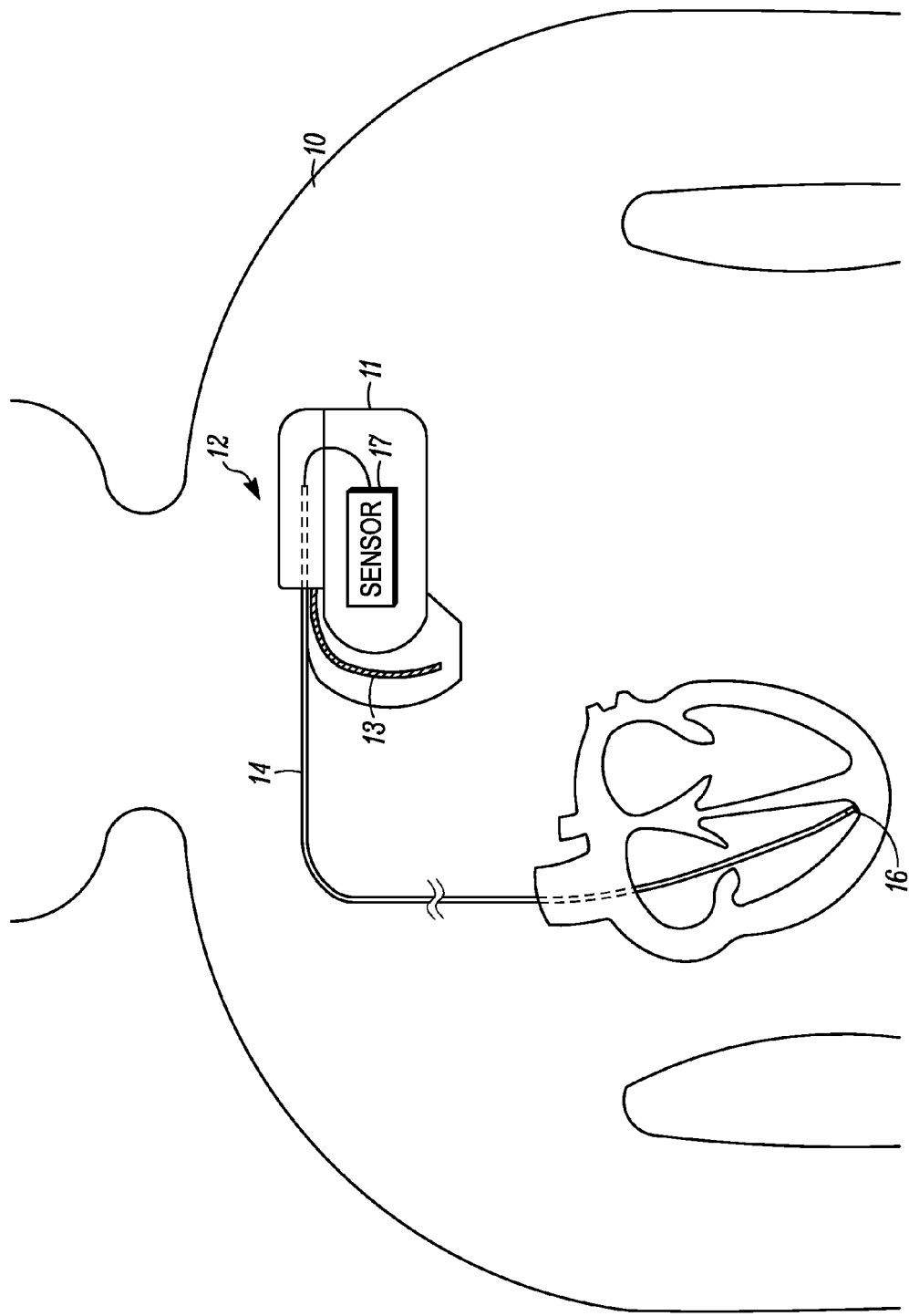
FIG. 1 is a schematic representation of an implantable medical device in a patient.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

As mentioned above, many implantable medical devices are configured to transmit information from the implantable device to a computer or other device located outside of the patient.

Some IMDs are configured to be capable of radio frequency (RF) transmission of data. RF data transmission can require a receiver very near to the IMD to receive the transmitted signal, or RF data transmission can communicate over moderate distances, such as within 9 to 12 feet. Distances less than 500 feet (152 meters) will be considered herein to be within a short-range telemetry communication range.

It is desirable to provide communications from an IMD over a greater distance than a short-range telemetry communication range. To accomplish this, a device constructed according to the principles of the present invention is configured to communicate with a pervasive wireless communication network. By establishing a communication link with a pervasive wireless communication network, longer range communications are enabled. Generally, a pervasive wireless communication network is a communications network that can be used to directly communicate with a host computer without the need for a repeater device. A pervasive network includes those networks that are sufficiently prevalent or dispersed that an average person in the U.S. would be within range of interfacing with the network at some point during a normal daily routine. A pervasive wireless network typically has a relatively broad effective geographic span. There are many different usable pervasive wireless communication networks. One example is a wireless telephone network, such as a cellular telephone network. Other example embodiments of a pervasive wireless communication network include a wireless pager network, wireless wide area networks (WAN) such as those installed in certain public places like coffee shops, airports, schools, or municipalities, and wireless local area networks (LAN) including those following the standards set forth by the Institute for Electrical and Electronic Engineers (IEEE) in Standards 802.11(b) and (g).

An IMD configured to communicate over a pervasive wireless network may be further configured to also communicate over a RF transmission link within a short-range telemetry communication range. There may be certain advantages to communicating over a short-range RF transmission communication link when one is available. For example, a short-range RF transmission communication is typically more reliable, more secure, and consumes less power. A short-range RF link is provided for communicating between the IMD and an external local device configured to receive short-range RF transmissions, such as the patient monitor device mentioned above.

One of the concerns with enabling communication from an IMD over a pervasive wireless communications network, such as a cellular telephone network, is the drain on the battery of the IMD. A typical cell phone chipset consumes a few Watts of power when transmitting. Some common medical device batteries such as $Li/MnO_2$ and Li/SVO batteries can deliver these power levels, but they typically only contain enough energy to operate at these power levels for a few hours of cumulative time, even when not accounting for the power drain of other circuitry in the IMD. Some common medical device batteries that have been engineered for long life, such as $Li—(CF)_x$ batteries, are not capable of these power levels in the sizes typically used in medical devices.

To address this power concern, one embodiment of an IMD incorporates a secondary rechargeable battery to power the communications over the pervasive wireless network in addition to a primary battery. In this embodiment, the secondary rechargeable battery supports only the communications over the pervasive wireless network, while the primary battery supports the other components of the IMD, including the short-range RF communications capabilities. The critical device functionality of the IMD, such as providing therapy to a patient, is therefore not compromised even if the rechargeable battery runs down. Patient compliance concerns are therefore mitigated because only the communications capabilities over the pervasive wireless network will be compromised by the patient failing to re-charge their IMD rechargeable battery.

In addition, an IMD according to the present invention provides at least two separate transmission paths. In one embodiment, a first communications unit with a first transmitter is powered by the primary, non-rechargeable battery and facilitates short-range communication with an external local transceiver that is located within a short-range telemetry communication range of the IMD. This first communications unit is used for routine monitoring communications with a host computer, as well as for emergency communications when necessary. This first communications unit is optimized for low power operation. Where possible, hard circuitry is provided to process the data instead of general purpose processors as will be discussed further herein. The use of hard circuitry results in a less flexible architecture than if general purpose processors were used for all data handling in the first communications unit. However, the use of hard circuitry where possible minimizes the power needs of the first communication unit.

A second communications unit with a transmitter/receiver unit is used for communications with a pervasive wireless network, such as a cell phone network. The second communications unit includes a transceiver for communication with a pervasive wireless network. The second communications unit is only provided with power when it has been determined that a communication should occur using the second communication unit. A third communications unit is also provided that is capable of inductive communications, in some embodiments, as will be discussed in further detail herein.

In some IMD systems described in past patent publications, a single transceiver was described as accomplishing both short-range RF telemetry communications and communications with a cellular phone network. While such a system is flexible and may minimize the number of components within the IMD, it has the disadvantage that a relatively power-hungry transceiver and associated chipset is used for even short-range RF communications.

An example embodiment of an implantable medical device 12 implanted in a patient 10 and including a housing 11 is depicted in FIG. 1. In some examples, the implantable medical device 12 also includes an antenna 13 for facilitating wireless communications with a host computer outside of the patient's body 10. The implantable medical device according to the present invention can be any number of devices including those that provide cardiac rhythm management, physiological monitoring, drug delivery, and/or neuromuscular stimulation. Exemplary implantable cardiac rhythm management devices include pacemakers, cardioverter/defibrillators, and cardiac resynchronization therapy devices. While various aspects of the present invention can be applied to a number of medical devices, for discussion purposes the medical device 12 is illustrated and described as a cardiac pacemaker. In one embodiment, the IMD 12 is configured to provide cardiac rhythm management and, as such, is configured with leads 14. Leads 14 contact cardiac tissue at electrode 16. The IMD 12 also includes a sensor 17 capable of measuring a body characteristic and generating a data signal that is representative or descriptive of the measurement taken. In one example, IMD 12 includes a sensor 17 that generates a cardiac activity signal. In another embodiment, the sensor 17 is an impedance sensor capable of determining a patient's respiration activity. Many other sensors 17 are usable and are known in the art. In some embodiments, IMD 12 is a therapy device that determines an appropriate electrical pulse therapy in response to a condition detected by sensor 17 and delivers the appropriate electrical pulse therapy to two or more implanted electrodes 16.

Data from sensor 17 is processed to determine a characteristic of the data. In some cases, when the data from sensor 17 is processed, it is determined that an abnormal or even dangerous situation exists. In one embodiment, this data signal is analyzed to reveal a medically significant event that merits that the patient receives immediate medical attention. For example, if the data signal from the IMD indicates the presence of a myocardial infarction or an upcoming de-compensation incident, this situation is identified as a significant medical event and the patient should seek immediate medical attention. Another medically significant event that is identified in one embodiment is the delivery of a defibrillation shock to the patient. Delivery of multiple shocks is a medically significant event in one embodiment. Sometimes the medically significant event merits seeing a physician within 24 hours.

In one embodiment, a processor of the IMD is further configured to identify a significant device event that threatens correct operation of the implantable medical device. Examples of a significant device event include a system fault, a significant change in impedance of implanted leads, and failure of a self-test. A significant change in impedance of implanted leads is a change that corresponds to a lead fracture or a crack or breakdown of insulation for a particular configuration of the implantable medical device.

Further examples of a significant device event include an end of life battery state or the device being in a non-therapy mode. Devices are sometimes purposely placed in a non-therapy mode because of the patient's medical procedures. For example, if a patient with an implanted cardiac re-synchronization device undergoes surgery where electrocautery will be used, the device is placed in a non-therapy mode so that the electricity of the electrocautery is not misinterpreted by the device to be cardiac signals, possibly causing unnecessary therapy. There are other examples of medical procedures that warrant placing an IMD in non-therapy mode. It is possible for an IMD to accidentally remain in non-therapy mode after the medical procedure. While in non-therapy mode after the medical procedure, the device cannot assist a patient who is experiencing a significant medical event.

Significant medical events and significant device events are two examples of significant events that warrant attention to the situation for the well-being of the patient.

Figure 2:
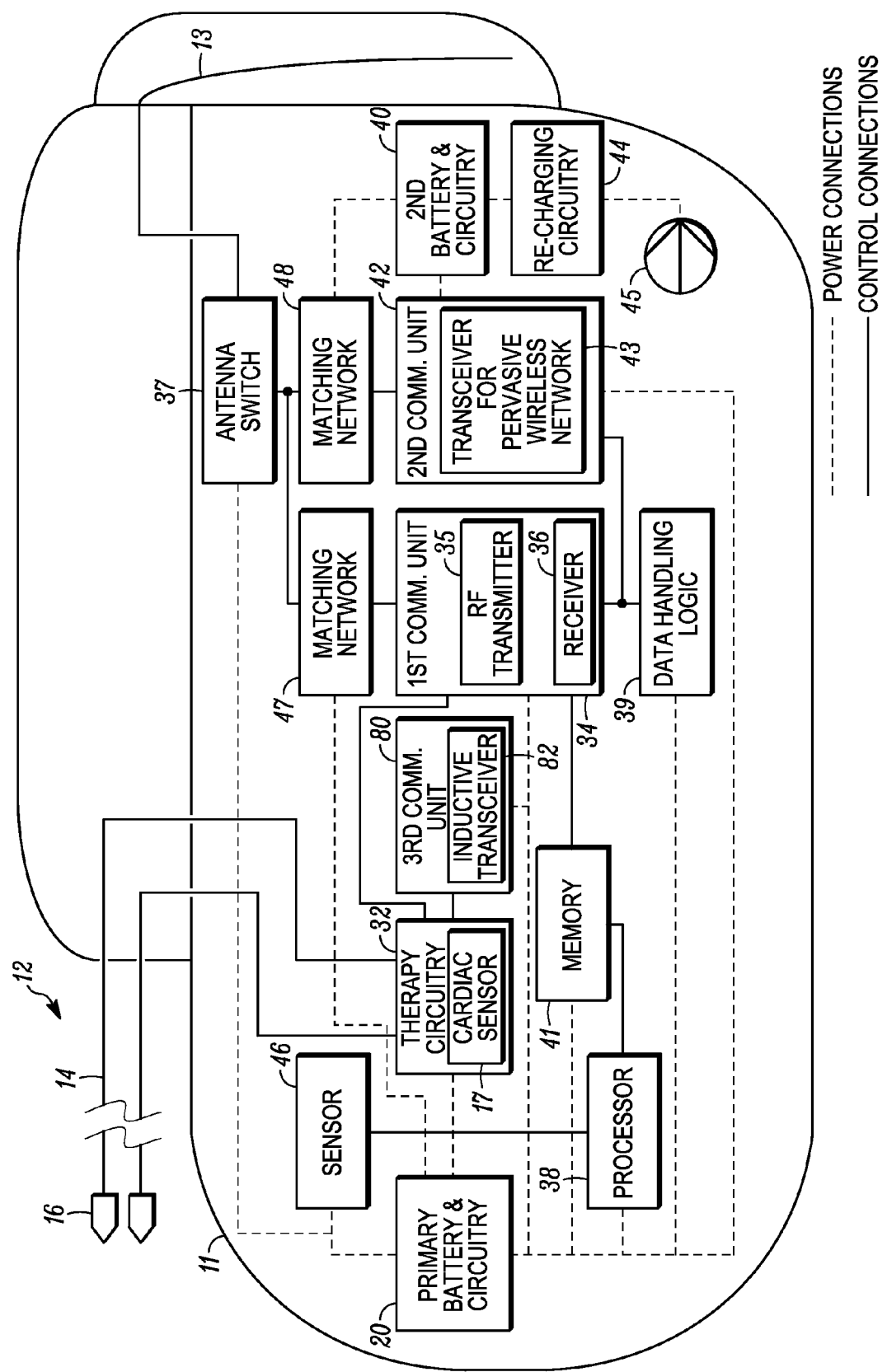
FIG. 2 is a schematic of components of an embodiment of an implantable medical device.

FIG. 2 illustrates one example of an IMD with power management features. The IMD is provided with two separate power sources to provide power to three separate communication units. In the embodiment of FIG. 2 the first communication unit is optimized for low power communications within a short-range telemetry communication range, and a separate second communication unit is provided for communication over a pervasive wireless network such as a cell phone network. In addition, a third communication unit is provided for near-field RF, or inductive, communications. In FIG. 2, solid lines show control and communications connections between the components, while dashed lines indicate power connections. A first non-rechargeable power source 20 is provided that is configured to power a first communication unit 34 and other IMD components, including processor 38, therapy circuitry 32 which includes cardiac sensor circuitry 17, an antenna switch 37, data handling logic 39, and memory 41.

In one embodiment, the first communication unit 34 is a short-range RF transmission communication unit and includes a short-range RF transmitter 35. In some embodiments, the first communication unit also includes a short-range RF receiver 36. In some embodiments, the transmitter and receiver are combined in a short-range RF transceiver. In some embodiments, the first communication unit 34 is an inductive communications unit. In other embodiments, the first communications unit uses an acoustic or ultrasonic link to communicate with another device, which is either implanted in the patient's body or in contact with the patient's skin. The other device may serve as a repeater for the communications from the first communications link. Examples of apparatuses and methods for ultrasonic wireless communication with an implanted medical device are described in U.S. Published Patent Application 2006/0009818, titled METHOD AND APPARATUS OF ACOUSTIC COMMUNICATION FOR IMPLANTABLE MEDICAL DEVICE, which is hereby incorporated herein in its entirety for any purpose.

In one embodiment, the IMD includes an additional sensor 46 that measures a body characteristic and generates a data signal representing the body characteristic. The IMD components illustrated in FIG. 2 are not exhaustive, and the use of many other components is possible.

The first communication unit 34 is specially structured to conserve power during communications to an external local transceiver that is within a short-range telemetry communication range. The term short-range telemetry communication range refers to 500 feet (152 meters) or less. In some short-range telemetry communication systems, the range is 20 feet (6 meters) or less. For inductive transceivers, the telemetry range is about 0.5 to 6 inches (1 to 15 centimeters).

The first communication unit 34 receives information from either the sensor 17 or the processor 38 or both. A first wireless transmitter 35 of the first communication unit 34 handles the task of transmitting this data to an external local receiver or transceiver. In some embodiments, a first wireless receiver 36 receives data from an external local transmitter, such as confirmation of transmission and programming information to alter how the IMD functions. In other embodiments, the first communication unit 34 does not have a receiver. In yet other embodiments, the transmitter and receiver functions are served by a combined transceiver component within the first communications unit 34.

The first communication unit 34 is particularly designed to conserve power. In some embodiments, the first communication unit uses power-on protocols as described in U.S. Pat. No. 6,985,773, which is hereby incorporated by reference in its entirety. Other examples of power saving methods and wake-up protocols are described in U.S. Published Application Nos. 2005-0288738, 2005-0027329, and 2005-0240245, which are incorporated herein by reference in their entirety. Wake-up protocols may also be sued with respect to the second communication unit.

In addition, the components of the wireless transmitter and receiver are selected to minimize power use. For example, analog components, tailored digital components and hard-wired digital components are selected where possible in place of more general purpose, more power hungry digital processors. Aspects of the transmission and reception tasks are handled by different components of the first communication unit that can be referred to as layers.

Physical layer circuitry decodes the data being received and encodes the data being transmitted, determining if each data bit is a one or a zero. This physical layer circuitry is made of analog circuitry and hard-wired digital components in one embodiment, rather than utilizing a general purpose processor, in order to minimize the power use of the physical layer. The digital components are tailored to perform a specific logic task, so that they can operate as efficiently as possible for their purpose.

The physical layer provides the decoded data to the data link layer when receiving, and encodes data from the data link layer when transmitting. The data link layer checks the data for errors and assembles bits into frames for transmission, or disassembles frames into bits for reception. In one embodiment, the data link layer includes a more versatile processor, but also includes digital hard-wired components that handle some aspects of the data checking. Because the data link layer does not rely exclusively on the function of a processor and because the physical layer uses some analog components, the power use of the transmitter/receiver unit is minimized.

Next, the data is provided by the data link layer to the network layer. Here the frames of data are assembled into appropriate packets for transmission, or packets are disassembled into frames of data upon reception. This function is carried out by a processor. The network layer also adds addresses of a destination to packets to be transmitted.

Referring again to FIG. 2, second rechargeable power source 40 is provided that is configured to power a second communications unit 42, where the second communications unit 42 includes a transceiver and chipset 43 that provides for communications over a pervasive wireless communication network. For example, where communication over a cellular telephone network is desired, a cellular telephone chipset is included in the second communication unit.

A recharging circuit 44 and recharging transducer 45 are also provided to recharge second rechargeable power source 40. Recharging transducer 45 utilizes one of any of a number of known techniques for getting energy into a battery in an implantable medical device, such as inductive charging. Inductive charging techniques are taught, for example, in U.S. Pat. No. 6,553,263, which is hereby incorporated herein by reference in its entirety for any purpose. Alternatively, the rechargeable battery may be recharged by acoustic or ultrasonic charging. Ultrasonic charging systems for implantable medical devices are described in U.S. Pat. No. 7,283,874, owned by Boston Scientific Corporation, St. Paul, Minn., and which is hereby incorporated herein by reference in its entirety for any purpose.

In one embodiment, no power is provided to the second communication unit 42 unless the processor 38 determines that a communication will be made over the pervasive wireless network. During a communication over the pervasive wireless network, the second communication unit 42 is powered on for enough time to negotiate the communication link, up-load the relevant event information, and receive confirmation that it was received. The duration of the use of the second communications unit during such a communication is likely to be only a 10-60 seconds in many situations, or 10 to 30 seconds.

In one embodiment, no power is provided to the first communication unit 34 unless the processor 38 determines that a communication over the low power first communication unit will be made. In one embodiment, no power is provided to either communication unit until a specific telemetry link is about to be used.

The first communication unit 34 includes a wireless transmitter and a receiver, in one embodiment, capable of establishing a first communications link from the IMD to an external local transceiver by way of an RF signal. The external local transceiver is generally in signal communication with a host computer, and in some cases the external transceiver and the host computer may be housed in the same component. Thereby, when the first communication unit 34 is within a short-range RF telemetry communication range of the local transceiver, clinical data stored in the IMD may be transmitted to the host computer using the first communications link.

An IMD embodiment further includes an inductive communications link. FIG. 2 shows an example embodiment of the components of an IMD having an inductive communication link. The inductive communications link is provided by way of a third communication unit 80 that includes an inductive transceiver 82 for transmitting and/or receiving inductive communications.

Figure 4:
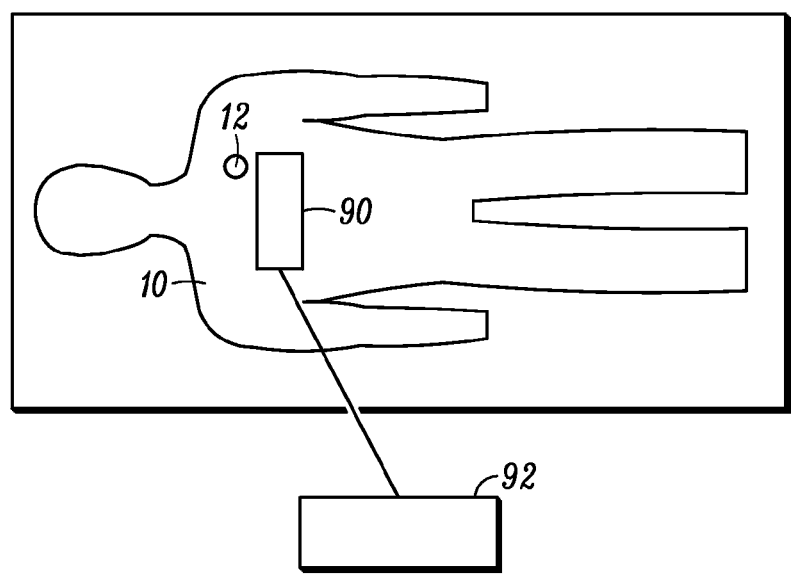
FIG. 4 is a depiction of a communication link between an implantable medical device and a computing device utilizing a wand.

An inductive communication link between an IMD and a computer is shown in FIG. 4. As discussed above, an inductive communication link is generally accomplished by placing a wand 90 over the patient's chest in a location that is proximate to the implantable medical device 12. The wand is in signal communication with a computing device 92. This signal communication may be wired or may be wireless. An inductive link is established between the IMD 12 and the wand 90, and the signal received at the wand 90 is then transmitted to the computing device 92.

This communication arrangement has the advantages of high security, because the signal from the IMD is too weak to be detected at more than a very short distance from the IMD. For example, in some embodiments an inductive communication link can be used for authentication and encryption key exchange prior to initiating a RF communication link. U.S. Pat. No. 7,228,182 describes cryptographic systems using an inductive link, and is hereby incorporated by reference in its entirety for any purpose. Moreover, there are certain countries where short-range RF communication links are not allowed or are limited based on that country's regulation of the electromagnetic spectrum. An inductive communication link allows communications to occur in such a situation.

Another benefit of having an inductive communication link capability available in an IMD is that it allows for another mode of communication with the IMD device if the other communication links are not available. For example, if in-band RF interferers are present, the inductive communication link could enable communications to occur. An inductive communication link also tends to consume relatively little electrical energy, and as such, can generally be powered from a primary battery, such as first non-rechargeable power source 20.

In one embodiment of an IMD, the IMD does not include short-range RF communications, such as RF communications for use with a patient monitor device placed in the patient's home. Instead, the IMD is configured with an inductive communication link, which is an inductive communication link, along with a pervasive wireless communications network link. In this arrangement, a patient with an IMD would not need to have a home-based patient monitoring device, thereby saving the cost of such a device. Emergency communications could occur over the pervasive wireless communication network as necessary, and routine communications could either occur over the pervasive wireless network or over the low-power RF or inductive communications links based on the availability of each.

A variety of data transmission protocols may be utilized to transmit data to and from an IMD over a pervasive wireless communication network. For example, General Packet Radio Service (GPRS), may be used, which is a global standard used, for example, by Blackberry devices. It is part of the Global System for Mobile Communications (GSM) standard. This can provide data rates of about 40 KBPS. Another option is Enhanced Data rates for GSM Evolution (EDGE) or Enhanced GRPS (EGPRS). Date rates of about 230 KBPS can be obtained by way of these protocols. Future communication protocols include Wideband Code Division Multiple Access (WCDMA), which may be able to support connections of several MBPS. In terms of operating frequencies, many GSM networks operate in the 900 MHz or 1800 MHz bands, and in the Americas they typically operate in the 850 MHz and 1900 MHz bands. Some implantable medical devices presently on the market have telemetry systems that operate at frequencies near these bands, such as at 870 MHz or at 914 MHz. It is possible to use the 1800 MHz and 1900 MHz band for medical telemetry, although tissue loss would be 4 to 5 dB higher at those frequencies.

In one embodiment, both the first communication unit 34 and the low power second communication unit 42 share the same single antenna 13. Efficient bio-compatible and bio-conformal antennas take up volume within or around the IMD, so this feature helps the IMD to minimize overall volume.

In one embodiment, the antenna is a broad-band, single mode antenna that has a bandwidth wide enough to cover both the frequency of the second communication unit, such as a cell-phone data connection, and the frequency of the low-power first communication link, such as an RF telemetry link. Such an antenna can efficiently cover both the 900 MHz ISM band and the 850 MHz GSM band because they are so close in frequency. Exemplary broad-band, single mode antennas are taught in commonly owned U.S. Pat. Nos. 6,456,256, 6,614,406, 6,809,701, which are incorporated herein by reference in their entirety for any purpose.

Figure 6:
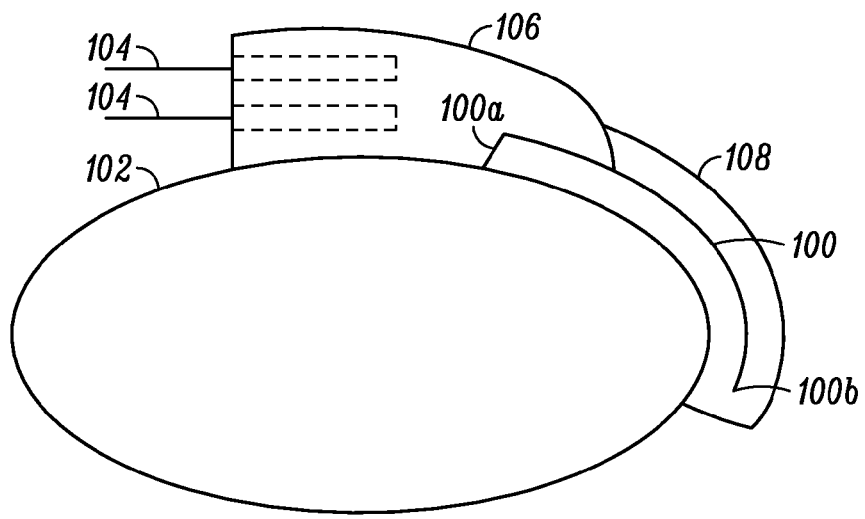
FIG. 6 depicts an embodiment of a broad-band single mode antenna for use with the present invention.

In one embodiment, a single band antenna is configured to receive and transmit electromagnetic radiation at frequencies from 800 MHz to 950 MHz. In a particular embodiment, the device is configured to receive and transmit electromagnetic radiation at frequencies from 900 MHz to 950 MHz for the short-range radio frequency link, and to receive and transmit at frequencies from 800 MHz to 900 MHz for the second communication link with the pervasive wireless communication network An example embodiment of a broad-band single mode antenna is depicted in FIG. 6. The depicted antenna is a circumferential antenna 100 that is suitable for radiating and receiving far-field electromagnetic radiation. The device housing 102 is metallic. One or more therapy leads 104 are connected to the circuitry contained within the housing by means of a header 106. The header 106 is a solid block structure made from a synthetic polymer that has feed-throughs therein for routing electrical connectors between the therapy leads 104 and the internal circuitry. The antenna compartment 108 is made of dielectric material and extends from the header 106 to wrap circumferentially around a curved portion of the device housing 102 with the antenna 100 embedded therein. The antenna 100 may be constructed of metal wire such as an alloy made of approximately 90% platinum and 10% iridium. Such a material is commonly used for feed-throughs of therapeutic leads and is both mechanically strong and biocompatible. This means that no welding or other means of attachment is required for attaching the antenna to the device and the antenna can be routed from the transmitting and receiving circuitry within the housing through the feed-through to the dielectric compartment with no interposing connections required. An alternative antenna and feed-through material is niobium, which has a slightly lower resistivity than the 90% platinum and 10% iridium alloy. In the embodiment shown in FIG. 6, the wire antenna 100 has a proximal end 100a that exits the device housing through a feed-through and begins its radiating length around the edge of the device, terminating at the distal end 100b.

In a different embodiment, the antenna is a dual-band antenna with two resonant modes. A dual-band antenna can efficiently cover both the 900 MHz ISM band and the 1900 MHz GSM band. Exemplary dual-band antennas are taught in commonly owned U.S. Pat. No. 7,047,076.

In one embodiment of a dual band antenna, the antenna is configured to receive and transmit electromagnetic radiation at a first mode having frequencies from 800 MHz to 950 MHz and at a second mode having frequencies from 1700 MHz to 2000 MHz. In a particular embodiment, the antenna is configured to receive and transmit electromagnetic radiation at frequencies in the first mode from 900 MHz to 950 MHz for the short-range radio frequency link. The antenna handles the second communication link with the pervasive wireless communication network either the first mode at 800 MHz to 900 MHz or the second mode at 1700 MHz to 2000 MHz.

Figure 7:
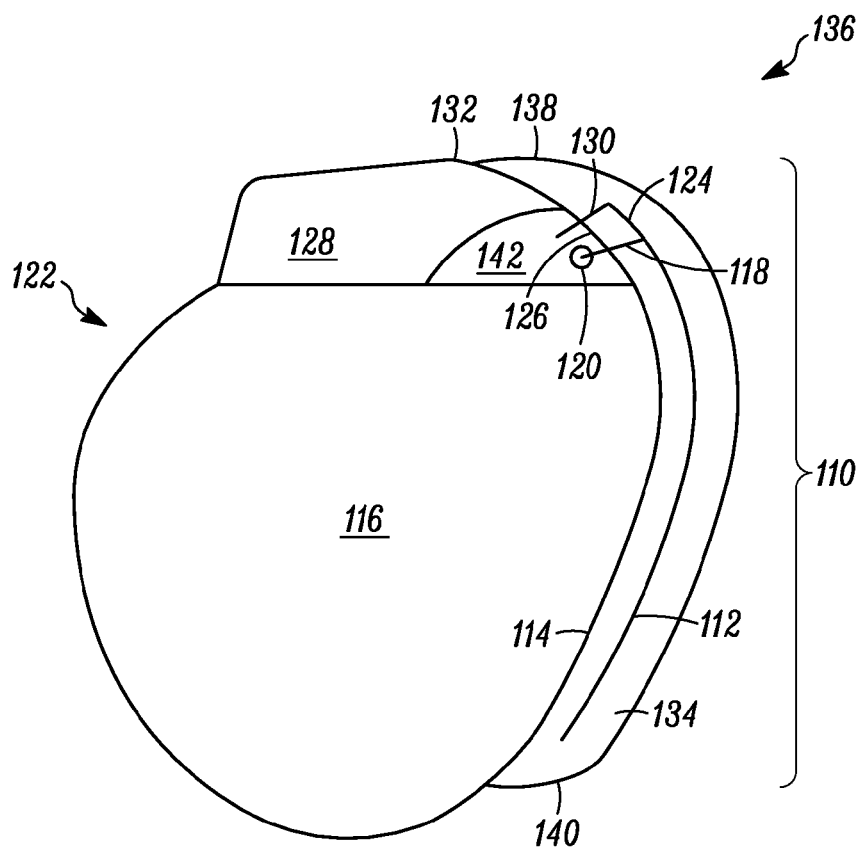
FIG. 7 depicts an embodiment of a dual band antenna for use with the present invention.

An example embodiment of a dual band antenna 110 is depicted in FIG. 7. Antenna 110 is an inverted-f antenna with a transmitting length 112 extending along a side 114 of body 116. Antenna 110 further includes a feed line 118 that passes through a feed-through 120 where it is electrically coupled to electronic circuitry within the housing 122. A cutout section 142 is provided to illustrate the connection between antenna 110 and housing 122. Further, the antenna 110 includes a shunt arm 124 that extends along a side 126 of the header 128 and that is electrically coupled to a conductive portion of the header 128 by a connector leg 130. A side 132 of the header 128 continues beyond the antenna 110.

While the feed-through 120 is shown in FIG. 7 as being in the header 128, in other cases, the feed-through 120 can be in an antenna radome outside of the header or some other portion of body 116. Further, in various embodiments the connector leg 130 can be electrically coupled at an electrically conductive portion of the header 128 or the body 116, depending upon the desired attachment location of the antenna 110. In some cases, the antenna 110 is constructed of one or more materials including, but not limited to, platinum, iridium, stainless steel, or combinations thereof such as platinum-iridium.

Antenna 110 may include special deployment procedures to limit the possibility of breaking or deforming the antenna 110. As shown in FIG. 7, antenna 110 is disposed within a dielectric housing 134 (also referred to as a dielectric compartment). The dielectric housing 134 can be formed of a dielectric material coating the antenna 110 in such a way that the transmitting length 112 is isolated a distance from the housing 122, and the antenna 110 is isolated from environmental conditions into which the medical device 136 is implanted or deployed. The dielectric housing 134 can be formed of any type of dielectric material, and where the medical device 136 is to be implanted in a human body, choice of the dielectric material may include biocompatibility considerations. Some examples of dielectric materials include polymers such as parylene, ecothane, tecothane, thermoplastic urethane, polytetrafluooethylene (PTFE), expanded polytetrafluooethylene (ETFE), and/or polytheretherketone (PEEK).

In embodiments where the medical device 100 is to be implanted in a patient, it may be desirable for medical device 100 to be as small as possible. This limited size may constrain the carrier frequencies that can be used if a quarter-wavelength monopole or half-wavelength dipole antenna is to be embedded with the device. Further, sharp edges may need to be avoided for patient comfort. Thus, for example, edges 138, 140 of dielectric housing 134 may be rounded, and/or brought into conformity with edges of housing 122 such that protrusions are avoided.

Figure 8:
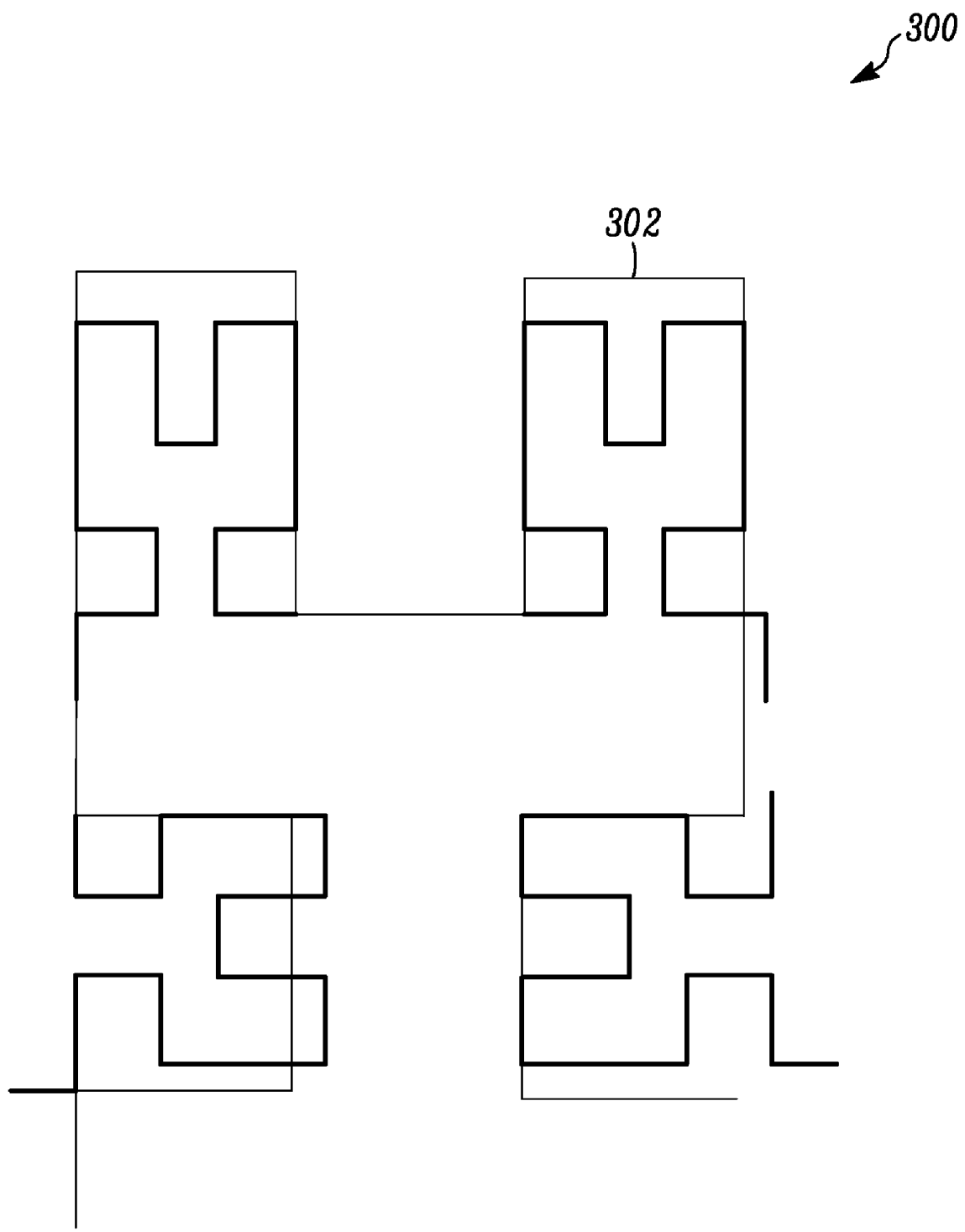
FIG. 8 is an embodiment of a fractal antenna for use with one embodiment of an IMD of the present invention.

An example embodiment of a multimode fractal antenna 300 is depicted in FIG. 8. This fractal antenna is described in detail in U.S. Patent Application No. 2007-0100385, which is incorporated herein in its entirety for any purpose.

In a preferred embodiment the fractal antenna is designed with a pattern such that its intrinsic impedance closely matches the RF circuitry in the implantable housing. This example minimizes the need for dynamically adjustable impedance matching circuitry as part of the implantable device, and the resulting device is simpler, more inexpensive and more reliable. In another preferred embodiment the fractal antenna is designed to have at least two transmission bands, such as at 400-450 MHz and 862-928 MHz, and not requiring a separate matching circuit for either band. In another preferred embodiment, the fractal antenna has a single signal feed point to obtain both of the two preferred transmission bands.

Fractal antennas typically have multiple resonant paths as a function of the repeating nature of the pattern, and thus are broadband radiators with multiple efficient transmission bands, while still being very compact and omni-directional. The small size is a function of the fractal pattern filling in the empty areas of the pattern with smaller sized copies of the larger pattern, thus having a space filling property that results in long antenna lengths in a small space or volume. In general, for a given surface area, the length of the antenna that can be placed in the given surface area improves at an exponential rate for each iteration of fractal pattern reduction, resulting in better antenna performance.

FIG. 8 illustrates how four small patterns may be placed to form the larger pattern 302 of the fractal antenna. This illustration shows how a repeating pattern on different scales may be used to form a fractal pattern, in which a series of different scale views of the pattern each reveal the same basic underlying structure. Such repeating patterns are how a fractal antenna may possess many resonance wavelengths.

Referring again to the embodiment of FIG. 2, the first communication unit 34 has a matching network 47 and the second communication unit 42 has a matching network 48. Both matching networks 47, 48 are connected to the antenna switch 37. The antenna switch 37 switches the antenna between the two communication units as controlled by the processor 38. The provision of separate matching networks allows optimal matching of each of the two communication units 34, 42. It is also possible for the first and second communication unit to share a single matching network. In this embodiment, the transmitter/receiver unit and the transceiver are optimized to have similar output impedances. Where differential output is present, the matching networks 47, 48 may include balans for differential to single ended conversion.

Figure 3:
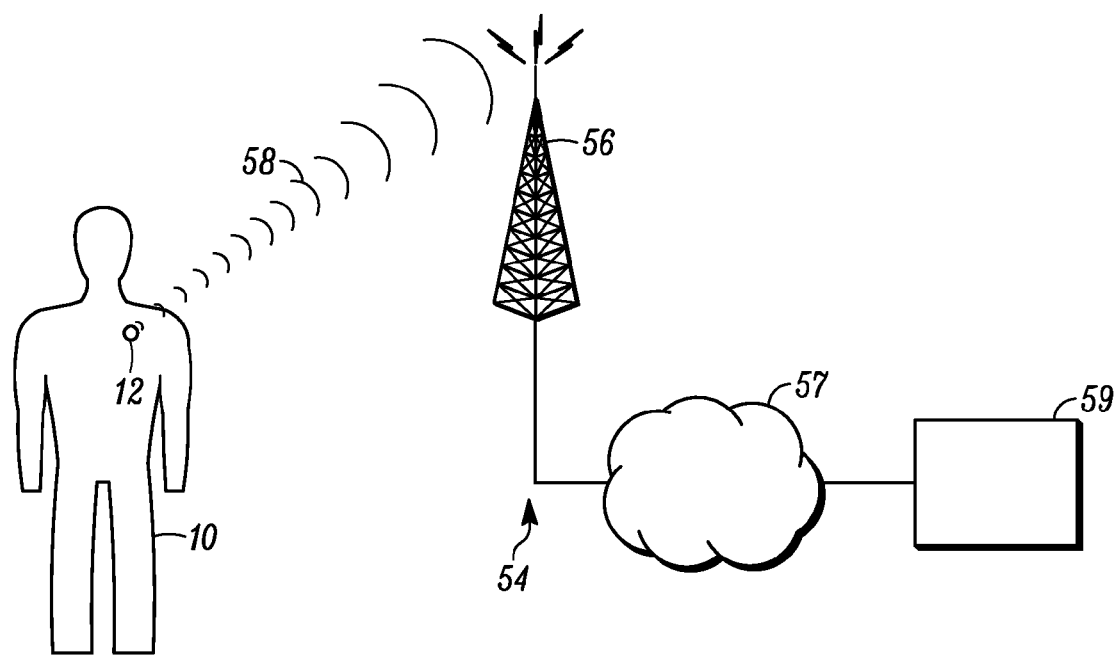
FIG. 3 is a depiction of a wireless communication network between an implantable medical device and a host computer over a pervasive wireless communication network.

An example embodiment of a communication network that includes an IMD is depicted in FIG. 3. In the embodiment of FIG. 3, an IMD 12 is implanted in a patient 10 and is configured to communicate over a pervasive wireless communication network 54. An IMD configured in this way includes at least one communication unit that is configured to transmit, and in some cases receive, wireless signals. A pervasive wireless communication network generally includes a network of antennas and transceivers across a geographic area, such as an antenna 56 configured to receive signals 58 transmitted from IMD 12. Signals received at antenna 56 are generally transmitted over a network 57 to a remote computer 59. Network 57 may comprise any of a number of communication networks, such as wireless or wired communication networks such as the internet. Remote computer 59 may comprise any of a number of computing devices, including servers, personal computers, or special purpose computers. Various additional aspects of the configuration and structure of a pervasive wireless network and communications with an IMD are disclosed in Published U.S. Patent Application 2004/0122489, which is incorporated herein in its entirety for any purpose.

Figure 5:
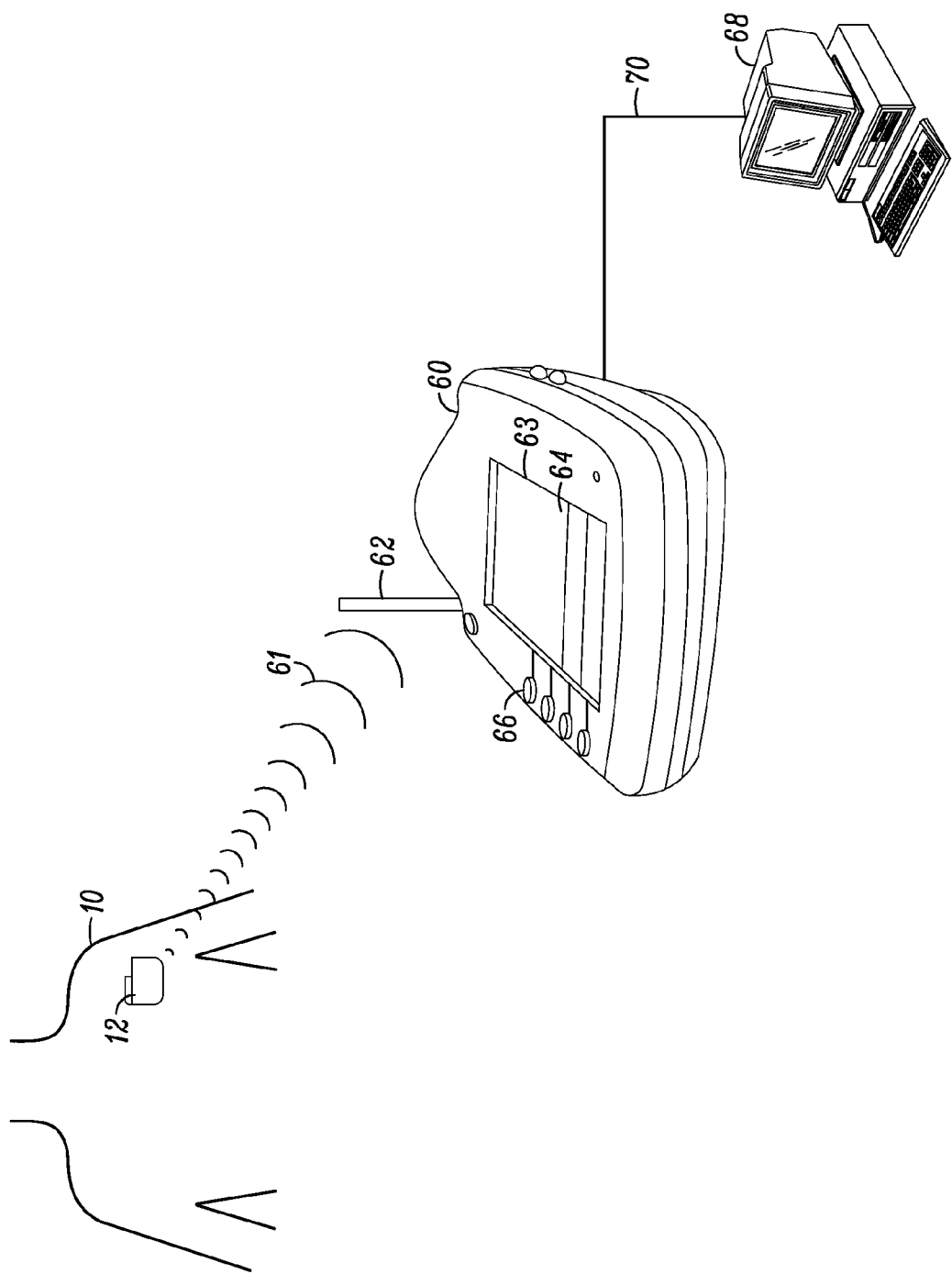
FIG. 5 depicts a wireless communication transmission from an implantable medical device when a patient is located near a patient management device.

In the embodiment of FIG. 2, the IMD includes both the capability of communicating over a short-range RF communication link (by way of first communication unit 34) and over a pervasive wireless communication link (by way of second communication unit 42). In one embodiment, the short-range RF communication link is utilized for any communications, whether routine or emergency in nature, when the short-range RF communication link is available, such as when the patient is located within range of a patient management device. For example, as depicted in FIG. 5, when a patient 10 is within the patient's home and within sufficient proximity to a patient management device 60, then RF signals 61 can be transmitted from the IMD 12 to the patient management device 60. The RF signals 61 are received by an antenna 62 of the patient management device 60, which also includes a patient interface 63. The patient interface 63 includes display screen 64 for displaying information and requesting input from the patient. The patient may provide input via patient input devices 66 or a touch sensitive screen. Exemplary patient management devices 60 include, but are not limited to, the LATITUDE® patient management system, the Model 2920 Programmer, and the Model 3120 Programmer, each available from Boston Scientific Corporation, Natick, Mass. Patient management device 60 is also capable of communicating with a remote computer 68 (also called a remote station 70) through telecommunications, such as over a conventional phone line 70, through cellular phone communications, or any other wired or wireless form of communication.

Some embodiments of the patient management device 60 do not include a patient interface or display screen. In these embodiments, the patient management device can behave purely as a repeater device, and thereby lower cost.

If emergency communications are necessary and the short-range RF communication link is not available, such as because the patient is out of range of the patient management device, then the link to the pervasive wireless communication network is used. For example, as seen in FIG. 3, the patient 10 is located away from home and so an emergency transmission is made from IMD 12 to antenna 56 of a pervasive wireless communication network. In another embodiment, the link to the pervasive wireless communication network is also used for routine monitoring communications when the short-range RF link is not available for a certain period of time. For example, if the patient has not been within range of the patient management device within 24 hours, then the pervasive wireless communication network will be utilized for routine monitoring communications. Other time periods are usable.

In an embodiment, an IMD is configured to communicate over the pervasive wireless communication network for emergency communications such as to provide notification of a significant medical event or a significant device event.

The IMD could then utilize the pervasive wireless communication link to make an emergency communication of this information related to a significant medical event or a significant device event. The emergency communication may be transmitted to a remote computer or medical facility, where the content of the communication may be used to determine a response. In some cases, a remote computer may determine that the patient's life is at risk and take appropriate actions to dispatch medical personnel to treat the patient. In some other cases, a medical worker could receive the information and determine an appropriate response, such as calling the patient or the patient's physician. For non-emergency communications, the short-range RF link is generally utilized. For example, routine device updates and data downloads would be conducted over the short-range RF link. However, if the IMD has not been within range for establishing the short-range RF link for a certain defined period of time, such as 48 hours, then in one embodiment the pervasive wireless communication network link may be utilized.

In one embodiment, the link to the pervasive wireless communication network is utilized for non-emergency communications so long as the second rechargeable power source has at least a certain defined charge level. For example, the IMD may be configured to make non-emergency communications over the pervasive wireless network so long as the second rechargeable power source has at least 15 percent of its initial charge. Other percentages are usable, such as if the rechargeable power source has at least 25 percent, 10 percent, or 5 percent of its initial charge. After this charge level is reached, then non-emergency use of the pervasive wireless communication network is avoided and the pervasive wireless communication network link is used only for emergency communications.

In a further embodiment, if the rechargeable battery is discharged to a point where it is not capable of supporting a communication over a pervasive wireless network, and there is a need to make an emergency communication but the patient is not within range of the short-range RF communication link, then the first non-rechargeable battery may be used to establish a communication link through the pervasive wireless communication network. However, if the state of charge of the first non-rechargeable battery is below a certain pre-defined level, such as below 5 percent of its initial charge, such that establishing a link with the pervasive wireless communication network could cause insufficient energy to be available to operate the primary functions of the IMD for a sufficient period of time, such as the functions that provide cardiac pacing and therapy, then the communication is not made, in one embodiment. Other percentages are usable for this threshold, such as if the primary power source has at least 7 percent, 3 percent, or 1 percent of its initial charge.

In one aspect of the operation of an IMD having a pervasive wireless communication network link, it may be possible to determine the location of the patient when an emergency communication is transmitted. For example, if the pervasive wireless communication network link utilizes the cellular telephone network, it is possible for the cell phone tower equipment to determine the approximate location from which the communication signal is being transmitted by determining the angle and orientation of arrival of the signal. Other techniques are known in the art for determining the location of the origin of a cell phone transmission. By determining the location of the patient, it may be possible for emergency medical personnel to be dispatched to the patient's exact location in response to the emergency communication from the IMD in order to provide potentially life-saving medical treatment to the patient. For example, if the IMD determines that the patient is experiencing or is about to experience a heart attack, the IMD initiates an emergency communication over the pervasive wireless communication network, which upon receipt by emergency personnel, is used to determine the patient's location and to dispatch an ambulance to treat the patient.

A typical emergency communication over the pervasive wireless communication network would be expected to last about 10 seconds. The communication would only last as long as is necessary to negotiate the communication, upload the relevant information, and receive confirmation that it was received. It is advantageous to make such a communication as short as possible to minimize the amount of power consumed. However, for a communication that lasts about 10 seconds, it is estimated that if this communication was powered by the primary (typically non-rechargeable) IMD battery, it would reduce the operative life of the IMD battery by about a few days. This is a generally relatively small reduction in battery life given the multiple year projected life of the battery. Furthermore, power consumption may held to a minimum by having the pervasive wireless communication network capabilities powered up only when an emergency communication is being made. The pervasive wireless communication functions are generally not configured to have a stand by mode, such as is common in non-implanted devices for communicating with a pervasive wireless network, such as a cell phone, thereby further minimizing the power requirements of the device.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged" "arranged and configured" "constructed and arranged" "constructed" "manufactured and arranged" and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An implantable medical device for use in a patient management system, said implantable medical device comprising:
    a sensor capable of measuring a body characteristic and generating a data signal describing the measured body characteristic;
    a processor configured to analyze the data signal and configured to identify one or more significant events that warrant attention for the well-being of a patient;
    a first communications unit comprising a first wireless transmitter/receiver capable of establishing a first communications link with a host computer using an external local transmitter/receiver unit, when said first wireless transmitter/receiver unit is within a short-range telemetry communication range of said local transmitter/receiver unit, to deliver at least notification of the one or more significant events to said host computer using said first communications link;
    a second communications unit comprising a second wireless transmitter/receiver unit capable of establishing a second communications link with said host computer over a pervasive wireless communications network to deliver at least notification of the one or more significant events to said host computer over said second communications link; wherein said first and second communications units are housed within the implantable medical device; and
    a single antenna operatively connected to both the first and second communications units.

2. The device of claim 1 wherein the antenna is a dual mode antenna.

3. The device of claim 2 wherein the antenna is an inverted-f antenna.

4. The device of claim 1 wherein the antenna is a single mode antenna.

5. The device of claim 1 wherein the pervasive wireless network is a wireless local area network or wireless wide area network.

6. The device of claim 5 wherein the first communication link is a short-range radio frequency link.

7. The device of claim 6 wherein the antenna is a single mode antenna.

8. The device of claim 7 wherein the antenna is configured to receive and transmit electromagnetic radiation at frequencies from 800 MHz to 950 MHz.

9. The device of claim 8 wherein the device is configured to:
    receive and transmit electromagnetic radiation at frequencies from 900 MHz to 950 MHz for the short-range radio frequency link;
    receive and transmit electromagnetic radiation at frequencies from 800 MHz to 900 MHz for the second communication link with the pervasive wireless communication network.

10. The device of claim 6 wherein the antenna is a dual mode antenna.

11. The device of claim 10 wherein the antenna is configured to:
    receive and transmit electromagnetic radiation at a first mode having frequencies from 800 MHz to 950 MHz; and
    receive and transmit electromagnetic radiation at a second mode having frequencies from 1700 MHz to 2000 MHz.

12. The device of claim 11 wherein the antenna is configured to:
    receive and transmit electromagnetic radiation at frequencies in the first mode from 900 MHz to 950 MHz for the short-range radio frequency link;
    receive and transmit electromagnetic radiation for the second communication link with the pervasive wireless communication network in one of:
        the first mode at 800 MHz to 900 MHz, and
        the second mode at 1700 MHz to 2000 MHz.

13. The device of claim 1 further comprising:
    a first matching network operatively connected to the first communications unit and the antenna; and
    a second matching network operatively connected to the second communications unit and the antenna.

14. The device of claim 1 wherein the antenna is a fractal antenna.

15. The device of claim 1 wherein the one or more significant events comprise one or more significant medical events that merit medical attention including any of a myocardial infarction, cardiac signals indicating an upcoming de-compensation incident, and delivery of a defibrillation shock by the implantable medical device.

16. The device of claim 1 wherein the one or more significant events comprise one or more significant device events that threaten correct operation of the implantable medical device including any of a system fault, a significant change in impedance of implanted leads, an end-of-life battery state, a reset of the device, the device being in non-therapy mode, and failure of a self-test.

17. A method of telemetry between an implantable medical device used in a patient management system and a host computer, comprising:
    providing said implantable medical device comprising a sensor and an antenna;

measuring a body characteristic using the sensor and generating a data signal that describes the measured body characteristic;

analyzing the data signal and identifying one or more significant events that merit attention;

wirelessly transmitting over the antenna by a first communication unit from the implantable medical device to an external local transmitter/receiver unit in the host computer over a first communications link, when said implantable medical device is within a short-range telemetry communication range of said local transmitter/receiver unit, to deliver at least notification of said one or more significant events to said host computer using said first communications link; and when said implantable medical device is out of range of the local transmitter/receiver unit, wirelessly transmitting over the antenna notification of said one or more significant events from the implantable medical device to the host computer by a second communications unit over a pervasive wireless communications network; wherein said first and second communications units are housed within the implantable medical device.

18. The method of claim 17 wherein wirelessly transmitting over the pervasive wireless network comprises transmitting over a wireless local area network or wireless wide area network.

19. The method of claim 18 wherein wirelessly transmitting over the first communication link comprises transmitting over a short-range radio frequency link.

20. The method of claim 19 wherein
wirelessly transmitting over the first communication link comprises transmitting at frequencies from 900 MHz to 950 MHz; and
wirelessly transmitting over the second communication link comprises transmitting at frequencies from 800 to 900 MHz.

21. The method of claim 17 comprising:
receiving and transmitting electromagnetic radiation at a first mode having frequencies from 800 MHz to 950 MHz; and
receiving and transmitting electromagnetic radiation at a second mode having frequencies from 1700 MHz to 2000 MHz.

22. The method of claim 21 comprising:
receiving and transmitting electromagnetic radiation at frequencies in the first mode from 900 MHz to 950 MHz for the short-range radio frequency link;
receiving and transmitting electromagnetic radiation for the second communication link with the pervasive wireless communication network in one of:
the first mode at 800 MHz to 900 MHz, and
the second mode at 1700 MHz to 2000 MHz.

* * * * *